US012330327B2

(12) United States Patent
Higgins et al.

(10) Patent No.: US 12,330,327 B2
(45) Date of Patent: Jun. 17, 2025

(54) APPARATUS FOR MODIFYING BIOLOGICAL MATERIAL AND METHODS OF USE AND ASSEMBLY

(71) Applicant: Higgins Biotech, Inc., Albany, NY (US)

(72) Inventors: Stephen Higgins, Albany, NY (US); Paul Higgins, Schenectady, NY (US); Daniel Lannan, Derry, NH (US); Craig Higgins, Albany, NY (US)

(73) Assignee: HIGGINS BIOTECH, INC., Albany, NY (US)

( * ) Notice: Subject to any disclaimer, the term of this patent is extended or adjusted under 35 U.S.C. 154(b) by 731 days.

(21) Appl. No.: 17/450,708

(22) Filed: Oct. 13, 2021

(65) Prior Publication Data

US 2022/0113227 A1    Apr. 14, 2022

Related U.S. Application Data

(60) Provisional application No. 63/090,901, filed on Oct. 13, 2020.

(51) Int. Cl.
| B26D 7/01 | (2006.01) |
| B26D 1/02 | (2006.01) |
| G01N 1/04 | (2006.01) |
| G01N 1/28 | (2006.01) |
| A61B 17/3211 | (2006.01) |

(52) U.S. Cl.
CPC ............. *B26D 7/01* (2013.01); *B26D 1/02* (2013.01); *G01N 1/04* (2013.01); *G01N 1/286* (2013.01); *A61B 17/3211* (2013.01); *G01N 2001/2873* (2013.01)

(58) Field of Classification Search
CPC ............. B26D 7/26; B26D 2007/6878; B26D 2007/2657; B26D 2007/206; B26D 1/605; B26D 1/60; B26D 1/045; B26D 1/04; B26D 7/01
See application file for complete search history.

(56) References Cited

FOREIGN PATENT DOCUMENTS

| CN | 206287191 U | * | 6/2017 | |
| CN | 107328605 A | * | 11/2017 | ............... G01N 1/14 |
| CN | 108168979 A | * | 6/2018 | ............... G01N 1/286 |
| CN | 108481390 A | * | 9/2018 | ............... B26D 1/28 |
| CN | 106737953 B | * | 2/2019 | ............... B26D 1/151 |
| CN | 110524606 A | * | 12/2019 | |
| CN | 110733071 A | * | 1/2020 | |
| CN | 111331030 A | * | 6/2020 | |
| CN | 112109121 | * | 12/2020 | |
| CN | 111086036 B | * | 11/2021 | ............... B26D 1/08 |

(Continued)

*Primary Examiner* — Jennifer S Matthews
(74) *Attorney, Agent, or Firm* — HESLIN ROTHENBERG FARLEY & MESITI P.C.

(57) ABSTRACT

An apparatus for modifying biological material and methods of use and assembly. The apparatus includes a base, a frame coupled to the base, and an adjustable arm assembly coupled to the frame and positioned above the base. The adjustable arm assembly includes a positioning arm extending from a first arm end to a second arm end, where the first arm end is coupled to the frame, and where the second arm end extends away from the frame towards the base. The adjustable arm assembly includes a blade-coupling-member assembly coupled to the second arm end.

17 Claims, 16 Drawing Sheets

(56) References Cited

FOREIGN PATENT DOCUMENTS

| | | | | | |
|---|---|---|---|---|---|
| JP | 3835479 | B1 | * | 10/2006 | ............. B28B 11/12 |
| JP | 2014072493 | A | * | 4/2014 | |
| JP | 6008548 | B2 | * | 10/2016 | |
| KR | 20180102016 | A | * | 9/2018 | |

* cited by examiner

FIG. 15A

1202 — Providing an apparatus for modifying biological material. The apparatus includes a base, a frame and an adjustable arm assembly. The base includes first and second guide rails disposed on a top surface of the base and defining a slot therebetween. The slot extends in an X-direction. The frame includes first and second supports attached to the base and straddling the first and second guide rails. The frame further includes a crossbar extending between the first and second guide rails in a Y direction that is substantially perpendicular to the X direction. The adjustable arm assembly is attached to the crossbar. The arm assembly extends downward from the crossbar toward the base in a Z direction that is substantially perpendicular to an X-Y plane defined by the X and Y directions. The arm assembly includes a blade mechanically coupled to a lower end portion of the arm assembly.

1204 — Positioning a biological-material containment facility in the slot. The containment facility is operable to be guided by the first and second guide rails in the X direction.

1206 — Disposing a biological material on the containment facility.

1208 — Engaging the biological material with the blade.

1210 — Modifying the biological material in the X direction by moving the containment facility within the slot.

1212 — Modifying the biological material in the Y direction by traversing the adjustable arm assembly along the crossbar.

1214 — Modifying the biological material in the Z direction by adjusting the adjustable arm assembly to vary a distance of the blade above the base in the Z direction.

To FIG 15B

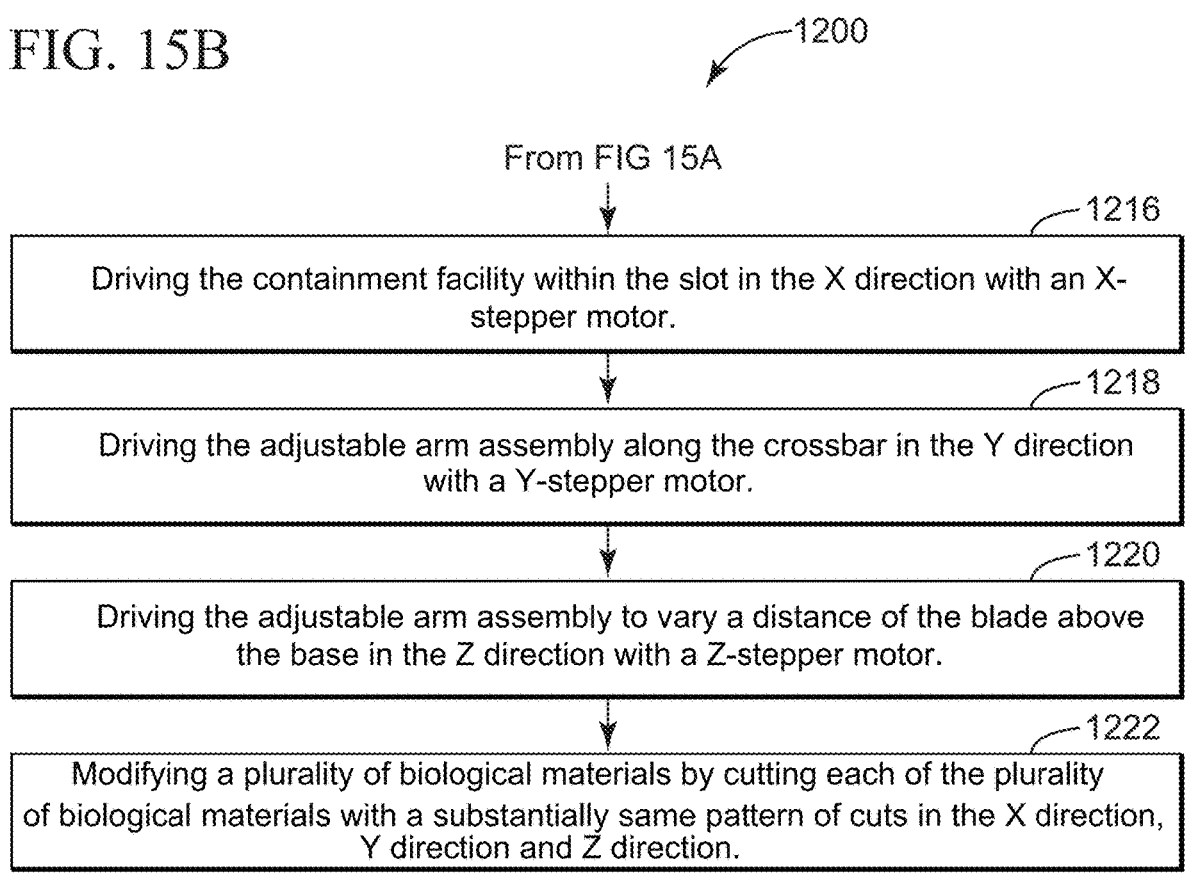

APPARATUS FOR MODIFYING BIOLOGICAL MATERIAL AND METHODS OF USE AND ASSEMBLY

TECHNICAL FIELD

The present invention relates generally to the field of biological research. More specifically, but not exclusively, the present invention relates to an apparatus and related methods for modifying biological material.

BACKGROUND

Various biological research processes are known in which modifications to biological material deposited or otherwise located on a dish, plate, slide, or other container may be beneficial in conducting scientific research or performing scientific experiments. Existing processes and methods used to perform such modifications often do not provide sufficient accuracy and precision for certain biological research processes. Thus, a need exists to improve existing processes for performing these modifications.

SUMMARY

Improvements to existing processes for modifying biological material are described herein. In particular, aspects described herein may improve precision and accuracy of various modifications performed to the biological material. Shortcomings of the prior art are overcome and additional advantages are provided through the provision of an apparatus for modifying biological material and methods of use and assembly.

An apparatus, in accordance with one or more aspects of the present disclosure, includes a base and a frame coupled to the base. Additionally, the apparatus includes an adjustable arm assembly coupled to the frame and positioned above the base, where the adjustable arm assembly includes a positioning arm extending from a first arm end to a second arm end. Further, the first arm end is coupled to the frame, and the second arm end extends away from the frame towards the base. The adjustable arm assembly also includes a blade-coupling-member assembly coupled to the second arm end.

Another apparatus in accordance with one or more aspects of the present disclosure, includes a base, a frame and an adjustable arm assembly. The base includes a first and a second guide rail, which are substantially disposed in parallel on a top surface of the base and which define a slot therebetween. A biological-material containment facility is configured to fit within the slot and is operable to be guided in an X direction by the first and second guide rails. The frame includes first and second supports, which are attached to the base and straddle the first and second guide rails. A crossbar extends between the first and second supports. The crossbar includes a Y-stepper motor that is mechanically coupled to a Y-lead screw. The Y-lead screw extends in a Y-direction that is substantially perpendicular to the X direction. The adjustable arm assembly is engaged with the Y-lead screw such that the arm assembly traverses in the Y direction when the Y-stepper motor turns the Y lead screw. The arm assembly includes a blade, which is operable to engage a biological material disposed on the containment facility. The blade is operable to modify the biological material in the Y-direction when the Y-stepper motor turns the Y-lead screw to move the arm assembly in the Y-direction. The blade is also operable to modify the biological material in the X-direction when the containment facility is moved within the slot in the X direction.

Further, a method in accordance with one or more aspects of the present disclosure, is provided for modifying biological material. The method includes selecting an apparatus and positioning a biological-material-containment facility that includes the biological material. The positioning includes aligning the biological material below a blade-coupling-member assembly of the apparatus. Further, the method includes modifying the biological material using a blade apparatus of the blade-coupling-member assembly.

Further, a method in accordance with one or more aspects of the present disclosure, includes assembling an apparatus, where the assembling includes providing components of the apparatus. The components of the apparatus include a base, a frame, and an adjustable arm assembly, where the adjustable arm assembly includes a positioning arm extending from a first arm end to a second arm end and a blade-coupling-member assembly. The assembling further includes coupling the frame to the base.

Another method, in accordance with one or more aspects of the present disclosure, includes providing an apparatus for modifying biological material. The apparatus includes a base, a frame and an adjustable arm assembly. The base includes first and second guide rails disposed on a top surface of the base and defining a slot therebetween. The slot extends in an X-direction. The frame includes first and second supports attached to the base and straddling the first and second guide rails. The frame further includes a crossbar extending between the first and second guide rails in a Y direction that is substantially perpendicular to the X direction. The adjustable arm assembly is attached to the crossbar. The arm assembly extends downward from the crossbar toward the base in a Z direction that is substantially perpendicular to an X-Y plane defined by the X and Y directions. The arm assembly includes a blade mechanically coupled to a lower end portion of the arm assembly. The method continues by positioning a biological-material containment facility in the slot. The containment facility is operable to be guided by the first and second guide rails in the X direction. A biological material is disposed on the containment facility. The biological material engages with the blade. The biological material is modified in the X direction by moving the containment facility within the slot between the first and second guide rails. The biological material is modified in the Y direction by traversing the adjustable arm assembly along the crossbar. The biological material is modified in the Z direction by adjusting the adjustable arm assembly to vary a distance of the blade above the base in the Z direction.

Additional features and advantages are realized through the concepts described herein.

BRIEF DESCRIPTION OF THE DRAWINGS

Aspects described herein are particularly pointed out and distinctly claimed as examples in the claims at the conclusion of the specification. The foregoing and other objects, features, and advantages of the disclosure are apparent from the following detailed description taken in conjunction with the accompanying drawings in which:

FIG. 15A depicts an example of a flow diagram of a method of modifying biological material, in accordance with aspects of the present disclosure; and FIG. 15B depicts an example of a continuation of the flow diagram of FIG. 15A, in accordance with aspects of the present disclosure.

DETAILED DESCRIPTION

Figure 1:
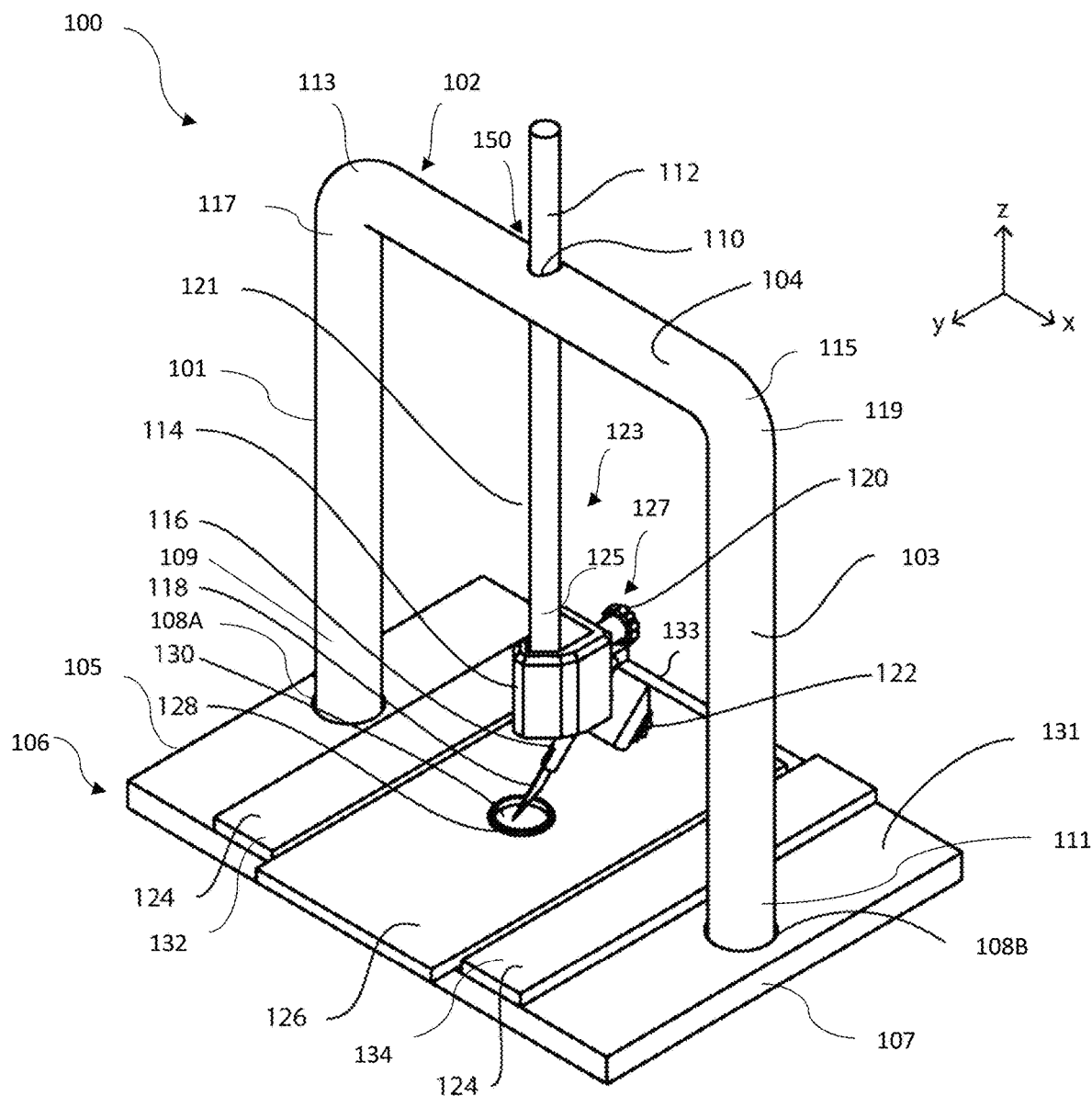
FIG. 1 depicts an example of a first perspective view of an apparatus for modifying biological material, in accordance with aspects of the present disclosure.
Figure 2:
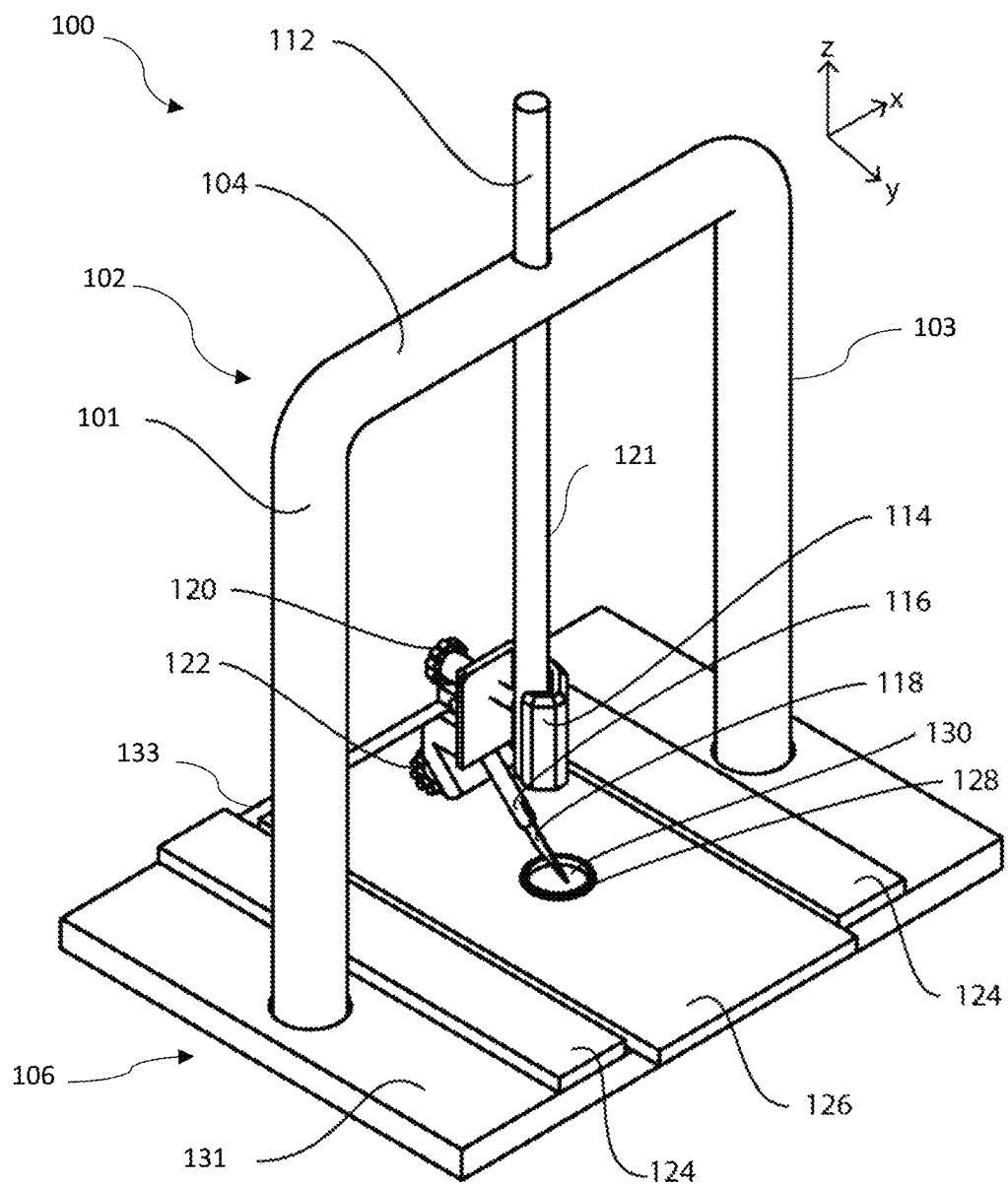
FIG. 2 depicts an example of a second perspective view of the apparatus of FIG. 1, in accordance with aspects of the present disclosure.
Figure 3:
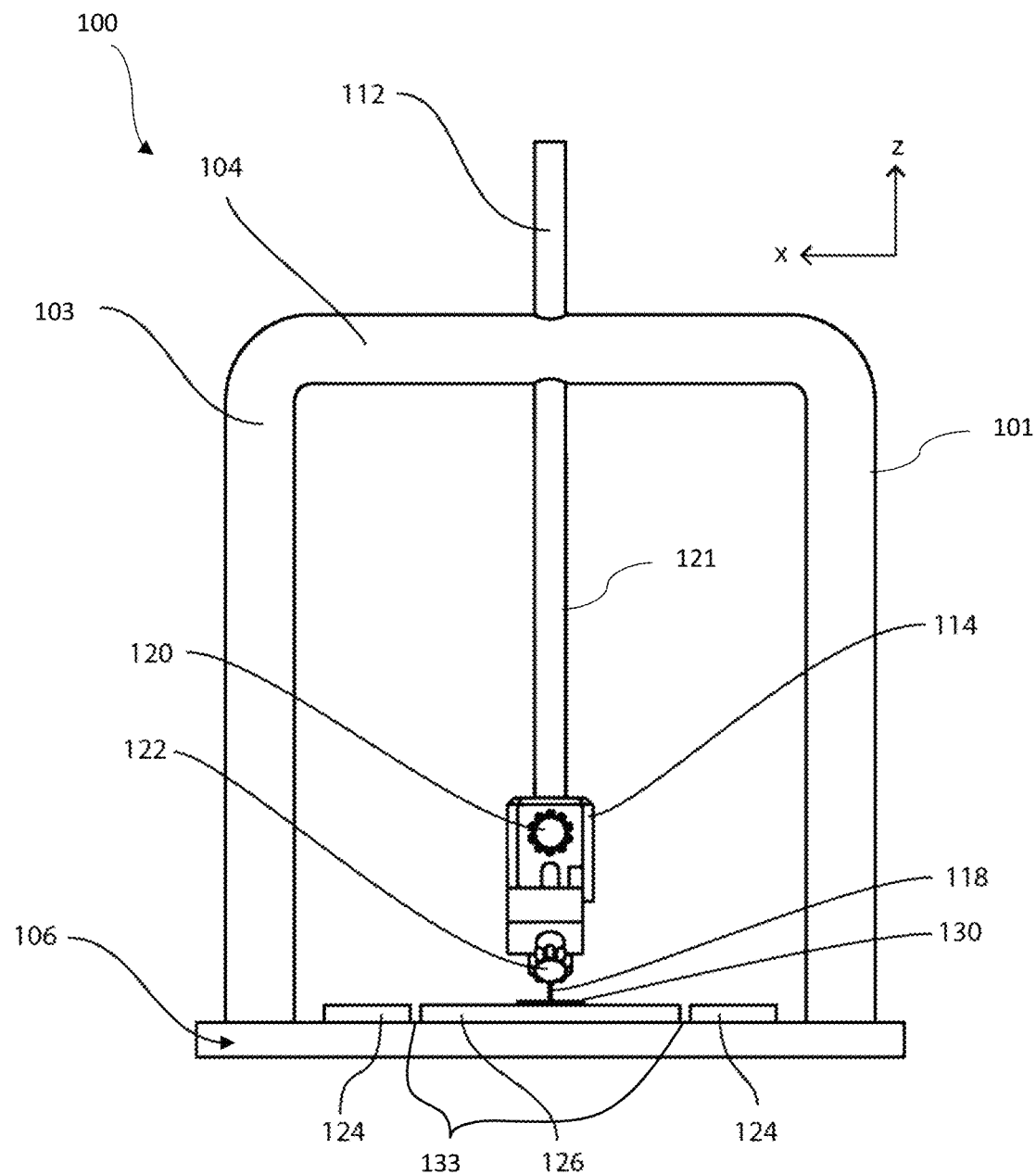
FIG. 3 depicts an example of an end view of the apparatus of FIG. 1, in accordance with aspects of the present disclosure.
Figure 4:
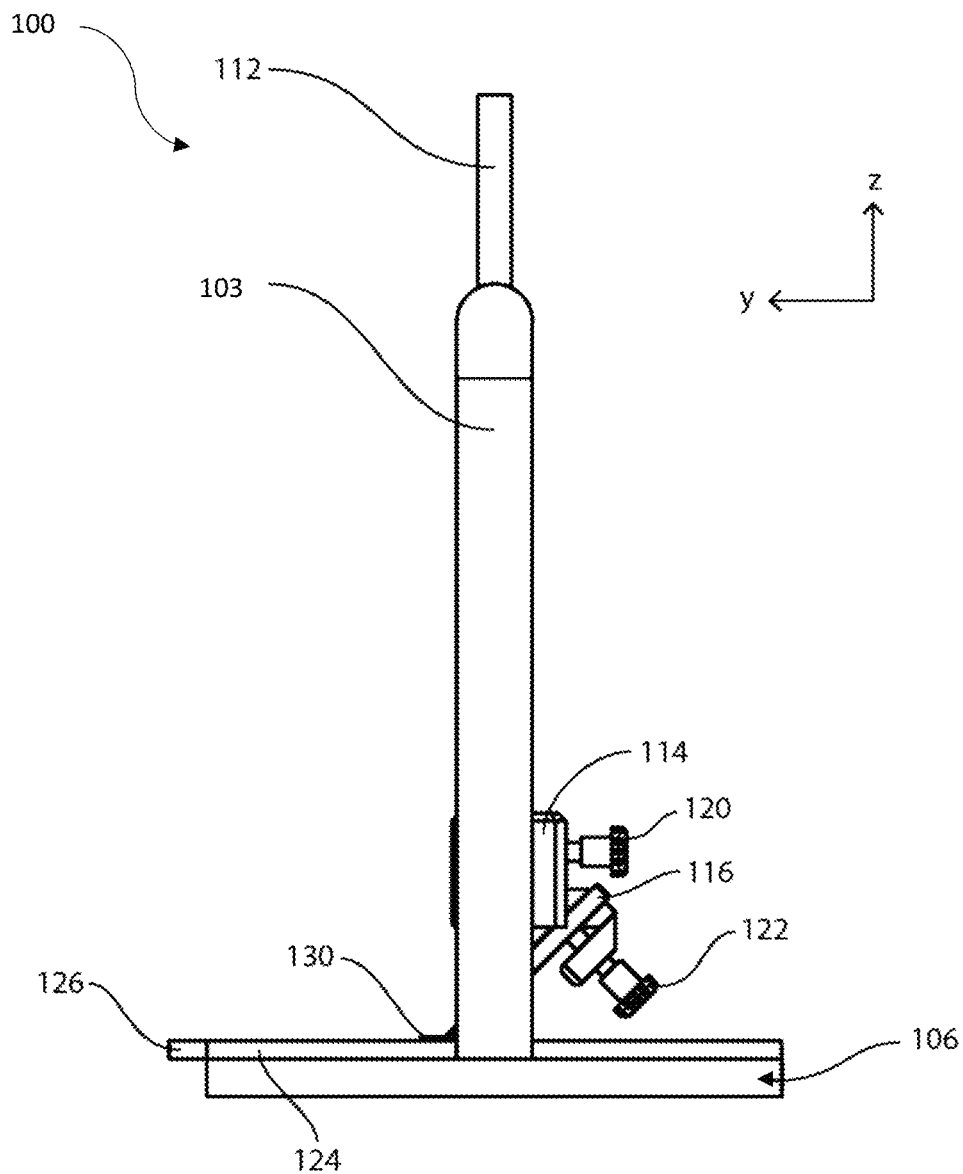
FIG. 4 depicts an example of a side view of the apparatus of FIG. 1, in accordance with aspects of the present disclosure.

Aspects of the present disclosure and certain examples, features, advantages, and details thereof, are explained more fully below with reference to the non-limiting examples illustrated in the accompanying drawings. Descriptions of well-known materials, fabrication tools, processing techniques, etc., are omitted so as not to unnecessarily obscure the relevant details. It should be understood, however, that the detailed description and the specific examples, while indicating aspects of the disclosure, are given by way of illustration only, and are not by way of limitation. Various substitutions, modifications, additions, and/or arrangements, within the spirit and/or scope of the underlying inventive concepts will be apparent to those skilled in the art from this disclosure.

Described herein is an apparatus for modifying biological material such as, for example, a biological sample or biological specimen (e.g., cells, tissue, blood, bone, skin, etc.), and associated methods such as, e.g., a method of use and a method of assembly. Performing modifications to biological material located upon or within a biological-material-containment facility, which may include any containment means used to hold biological material to be analyzed, is often desirable for various research or scientific experiments. Non-limiting examples of a biological-material-containment facility include a microscope slide, an analytic plate, a diagnostic dish, a sliderplate, a multiwell plate, a flask, a vessel, a tube, or other container. Example modifications to the biological material include, for example, wounding the biological material to determine the mechanistic underpinnings of wound healing. For instance, the apparatus may include a blade that is capable of excising or scratching biological material in a meaningful or useful way. Other mechanistic underpinnings that may be examined in response to modifying biological material may include cell migration/invasion as well as tumor development and metastasis.

Existing devices and methods used to modify biological material can be insufficiently precise and introduce inaccuracies to scientific experiments and research analysis. Advantageously, aspects disclosed herein provide, via an apparatus for modifying biological material, improved precision and accuracy when modifying biological material. Further, statistical evaluation of modifications to biological material can be improved by aspects described herein, thereby facilitating improved adaptations to in-vivo disease technology and treatment assessments.

Referring now to FIGS. 1-4, an embodiment of an apparatus 100 for modifying biological material is shown. The apparatus 100 may include a base 106 and a frame 102 coupled to the base 106. The frame 102 may include a first support 101 coupled to a first end 105 of the base 106 and a second support 103 coupled to a second end 107 of the base 106. The first support 101 and the second support 103 may include, for example, rods, posts, extruded rails, or other rigid bodies. Further, the first support 101 and the second support 103 may engage corresponding cavities 108A, 108B in the base 106, where the cavities 108A, 108B may be geometrically sized and shaped, or configured to receive, or otherwise capable of receiving a first end 109 of the first support 101 and a first end 111 of the second support 103. The first support 101 and the second support 103 may be affixed to the base 106 via, for example, one or more fasteners, brackets, clamps, adhesive material, or other connection means and combinations thereof.

The frame 102 may also include a crossbar 104 positioned or suspended above the base 106. The crossbar 104 may include a first crossbar end 113 supported by the first support 101 and a second crossbar end 115 supported by the second support 103. In one example, the first crossbar end 113 may be supported by a second end 117 of the first support 101 and the second crossbar end 115 may be supported by the second end 119 of the second support 103 (e.g. such that frame 102 is U-shaped). The crossbar 104 may be rigidly or adjustably attached to the first support 101 and the second support 103. For instance, the crossbar 104 may be connected to the first support 101 and the second support 103 using fasteners, screws, clamps, brackets, or other means of connection and combinations thereof. Alternatively, the frame 102 may be a one-piece construct. Further, the crossbar 104 may include one or more apertures 150 where at least one aperture 110 of the one or more apertures 150 may be geometrically sized and shaped, or configured to engage, or otherwise capable of engaging a first arm end 112 of a positioning arm 121. For instance, the at least one aperture 110 may include a channel or other conduit traversing the crossbar 104 that perpendicular to a length of the crossbar 104 and aligned with the first support 101 and the second support 103.

The apparatus 100 may further include an adjustable arm assembly 123 coupled to the crossbar 104 of the frame 102. The adjustable arm assembly 123 may include the positioning arm 121, where the positioning arm 121 extends from the first arm end 112 to a second arm end 125. In particular, the second arm end 125 may extend away from the crossbar 104 towards the base 106. According to one embodiment, the positioning arm 121 may include a cylindric, polygonal, or rail-shaped extruded body. Further, the second arm end 125 may be suspended a desired distance above the base 106 so that biological material may be positioned between the second arm end 125 and the base 106 for modification. The adjustable arm assembly 123 may further include a blade-coupling-member assembly 114 coupled to the second arm end 125 of the positioning arm 121. The blade-coupling-member assembly 114 may include a blade assembly 116 geometrically sized and shaped, or configured to modify, or otherwise capable of modifying biological material. For instance, blade assembly 116 may include a cylindrical or polygonal shaped extruded body such as, e.g., a precision knife. The blade-coupling-member assembly 114 may include a screw clamping fastener 122 capable of being affixed to the blade assembly 116 that may include, for example, a blade 118. The adjustable arm assembly 123 may also include one or more fasteners 127, such as screw clamping fastener 120, capable of fastening blade-coupling-member assembly 114 to the second arm end 125 of the positioning arm 121.

The base 106 may include a top surface 131 and a plurality of guide rails 124 located on the top surface 131. Further, the base 106 may include a slot 133 located between a first guide rail 134 of the plurality of guide rails 124 and a second guide rail 132 of the plurality of guide rails 124. According to one embodiment, the first guide rail 134 and the second guide rail 132 may be parallelly oriented to each other and perpendicular to the crossbar 104 of the frame 102. According to another embodiment, the plurality of guide rails 124 may be pivotable about an axis extending perpendicular to the top surface 131 of the base 106. According to one embodiment, the blade-coupling-member assembly 114 may be suspended above the slot 133, and the slot 133 may be geometrically sized and shaped, or configured to receive, or otherwise capable of receiving a biological-material-containment facility 126 that may include biological material. According to one embodiment, the biological-material-containment facility 126 may be a sliderplate or other slidable member that may include a dish cavity 128. Further, the dish cavity 128 may be geometrically sized and shaped, or configured to receive, or otherwise capable of receiving a dish 130 (e.g. a 35 mm dish), where the dish 130 may include circumscribed walls for retaining the biological material.

The biological material may be modified via utilization of a blade 118 of blade assembly 116. For instance, the blade 118 made be used to excise or scratch the contents of the dish 130 to facilitate scientific research and tissue experiments. In particular, a user may initially position the adjustable arm assembly 123 in a fixed position, and then the user may manually adjust the positioning of the biological-material-containment facility 126 in order to move the biological material relative to the blade 118. The biological material may be modified based on, for example, desired wound patterning. According to one embodiment, the biological-material-containment facility 126 may be rotated about an axis to a desired angle relative to the blade 118 or the frame 102.

Figure 5:
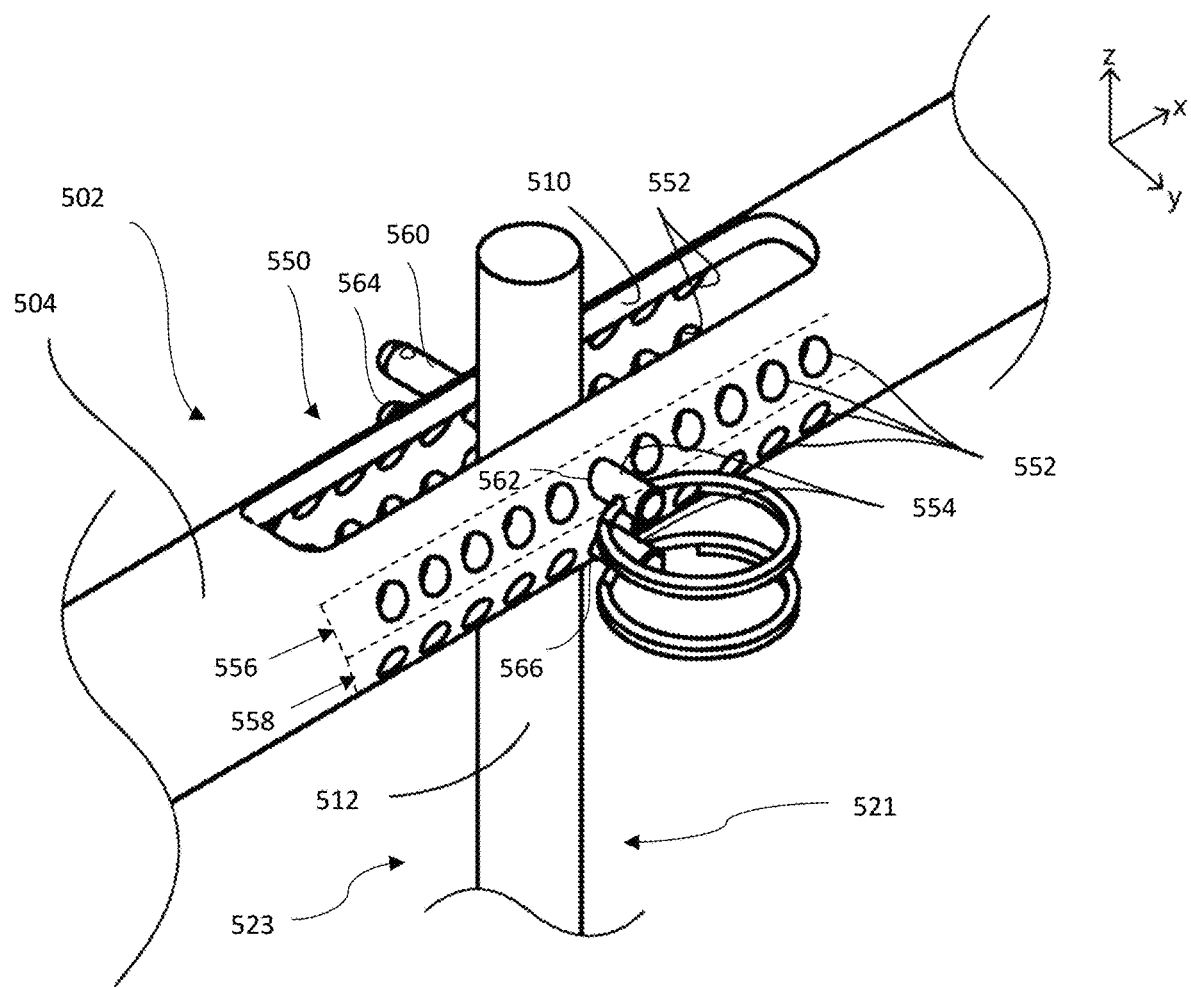
FIG. 5 depicts an example of a perspective enlarged view of an arm assembly and crossbar of an apparatus for modifying biological material, in accordance with aspects of the present disclosure.
Figure 6:
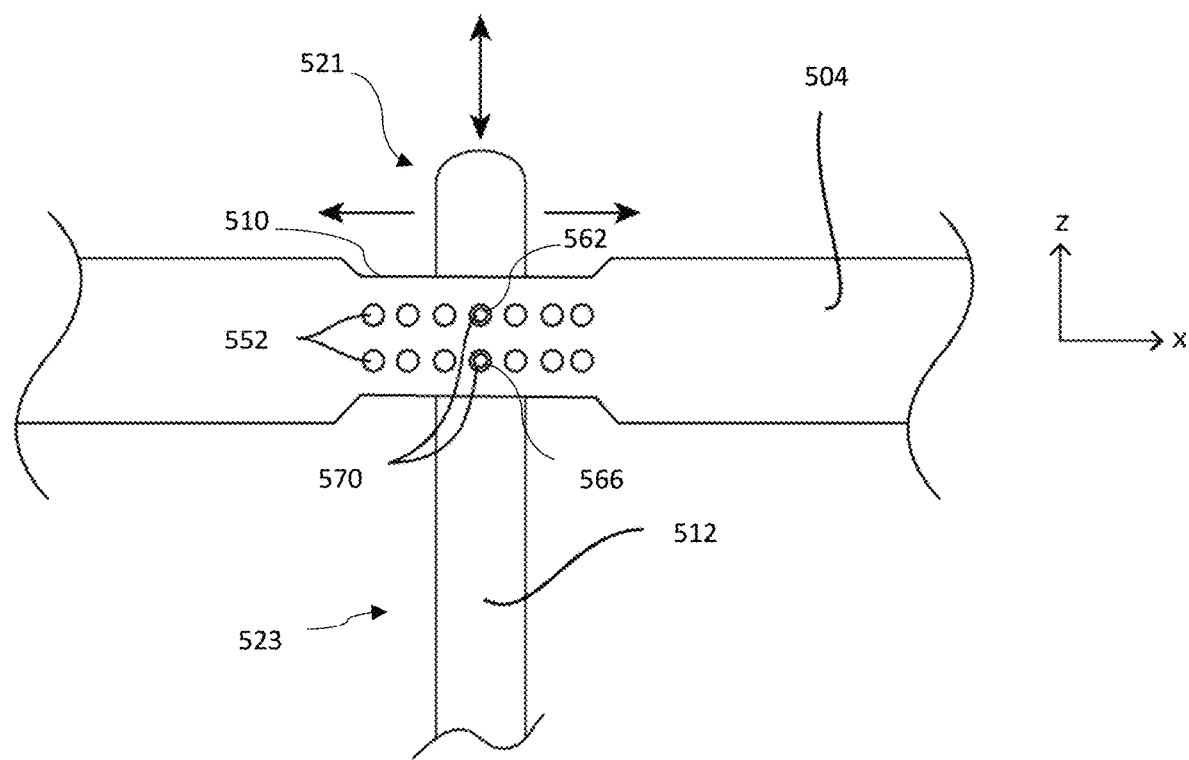
FIG. 6 depicts an example of an end view of the arm assembly and crossbar of FIG. 5, in accordance with aspects of the present disclosure.
Figure 7:
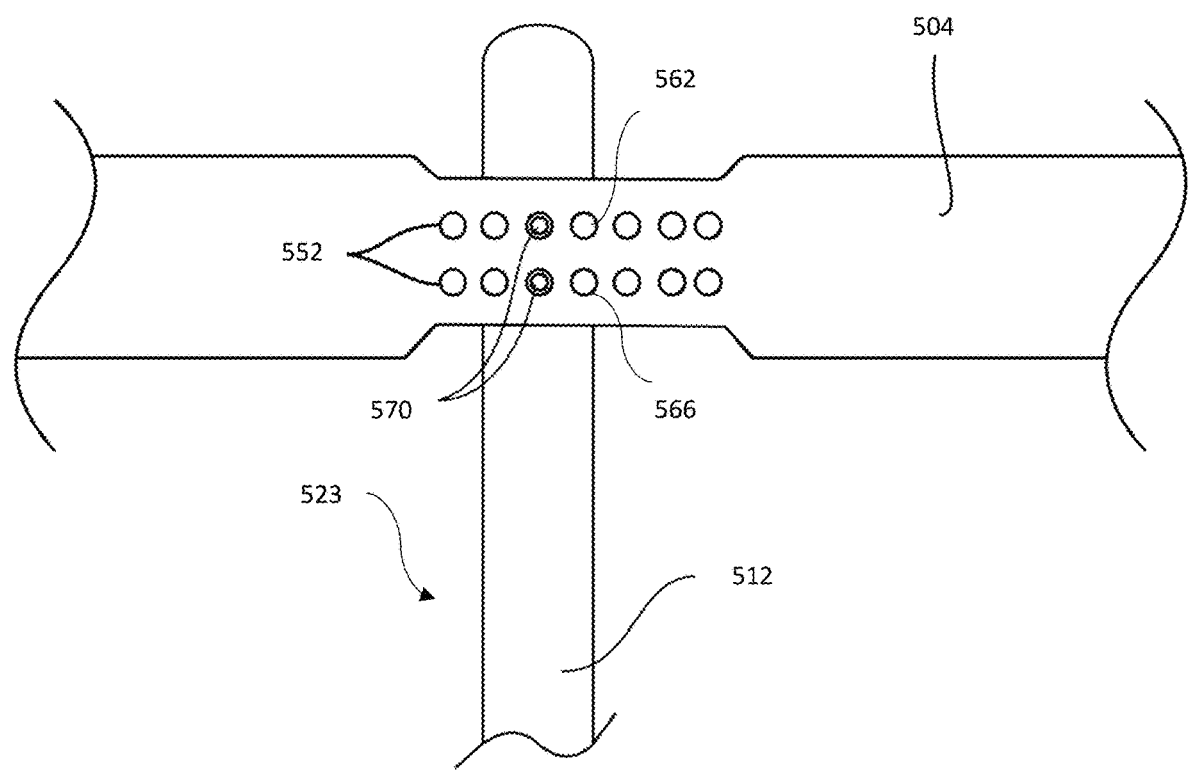
FIG. 7 depicts an example of an end view of the arm assembly and crossbar of FIG. 6 with the arm assembly having been shifted relative to the crossbar, in accordance with aspects of the present disclosure.

Referring now to FIGS. 5-7, embodiments of a frame 502 and adjustable arm assembly 523 are depicted. The frame 502 may include a crossbar 504 that may include one or more apertures 550. Further, the one or more apertures 550 may include a slot 510 (also referred to herein as channel 510) that may be geometrically sized and shaped, or configured to engage, or otherwise capable of engaging a first arm end 512 of a positioning arm 521 of the adjustable arm assembly 523. As depicted, the slot 510 may be a channel or other conduit extending longitudinally along a length of the crossbar 504 such that the location of the first arm end 512 of positioning arm 521 may be slidably adjusted within the slot 510. In particular, as shown in FIG. 6, the positioning arm 521 may be adjusted along the channel 510, with two degrees of freedom, laterally along the x-plane or adjusted vertically along the z-plane. According to one embodiment, the one or more apertures 550 may include a plurality of apertures 552 positioned in the crossbar 504 and oriented perpendicular to the channel 510, where each of the plurality of apertures 552 traverse the channel 510. The plurality of apertures 552 may include, for example, one or more pin holes, and each aperture of the plurality of apertures 552 may be geometrically sized and shaped, or configured to engage, or otherwise capable of engaging a fixation member 554, as shown in FIG. 5, where the fixation member 554 may be capable of fixating the first arm end 512 of the positioning arm 521 to the crossbar 504.

According to one embodiment, the plurality of apertures 552 may be arranged in a longitudinal array along the length of the channel 510. In particular, the plurality of apertures 552 may be aligned in a first row 556 of multiple apertures and a second row 558 of multiple apertures, where the first row 556 and the second row 558 extend longitudinally along the channel 510. As shown in FIG. 5, the first arm end 512 of the positioning arm 521 may be fixated to the crossbar 504 by a plurality of fixation members 554, where a first fixation member 560 of the one or more fixation members 554 may be coupled to an aperture 562 of the first row 556 and a second fixation member 564 of the one or more fixation members 554 may be coupled to an aperture 566 of the second row 558. The location of the positioning arm 521 may be adjustable within the channel 510 based on the positioning arm 521 being affixed to different apertures of the plurality of apertures 552. For instance, in comparing the adjustable arm assembly 523 of FIG. 6 to the adjustable arm assembly 523 of FIG. 7, the positioning arm 521 has been shifted such that the positioning arm 521 is affixed to different apertures of the plurality of apertures 552. Further, the plurality of apertures 552 may be spaced apart a pre-defined distance (e.g. every 3.5 mm if each aperture is 10 mm in diameter) such that each of the plurality of apertures 552 can receive a respective fixation member 554 (FIG. 5) without impeding the function or structural integrity of other apertures of the plurality of apertures 552.

Additionally, the positioning arm 521 may include multiple apertures 570 (FIGS. 6-7) extending through a body of the positioning arm 521, where the multiple apertures 570 (FIGS. 6-7) may be positioned at the first arm end 512 and each of the multiple apertures 570 (FIGS. 6-7) may be capable of receiving a corresponding fixation member of the one or more fixation members 554 (FIG. 5). For instance, a fixation member 554 (FIG. 5) may be inserted through an aperture of the plurality of apertures 552 of the crossbar 504 and through a corresponding aperture of the multiple apertures 570 (FIGS. 6-7) of the positioning arm 521 to fasten the first arm end 512 to the crossbar 504. The fixation members 554 may include a detent located along a shaft towards a distal end of the fixation member 554 whereby the detent provides a means for resisting displacement and holding the fixation member 554 in position within the plurality of apertures 552 and/or multiple apertures 570 (FIGS. 6-7).

Figure 8:
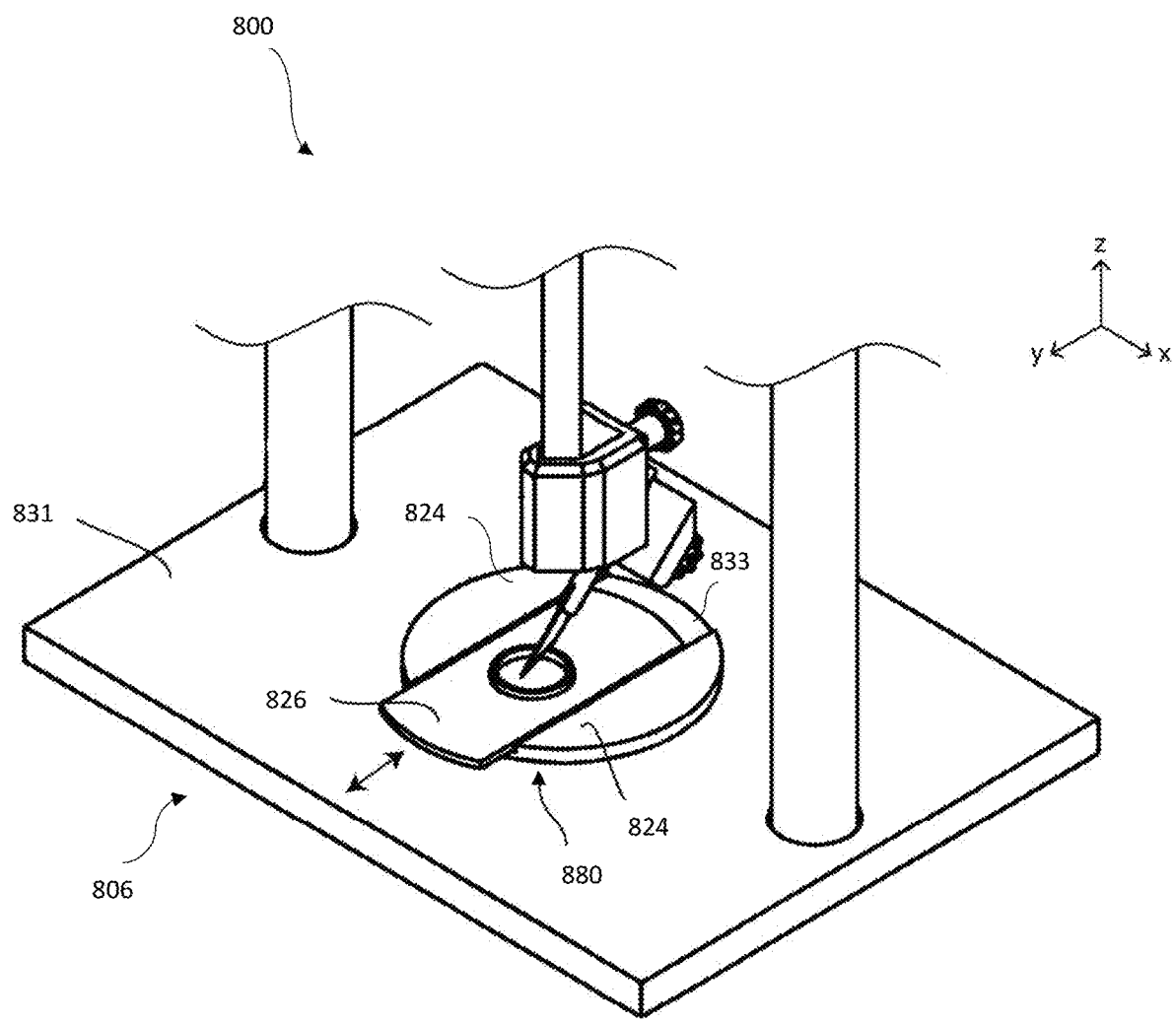
FIG. 8 depicts an example of a perspective view of a lower portion of the apparatus of FIG. 1, in accordance with aspects of the present disclosure.
Figure 9:
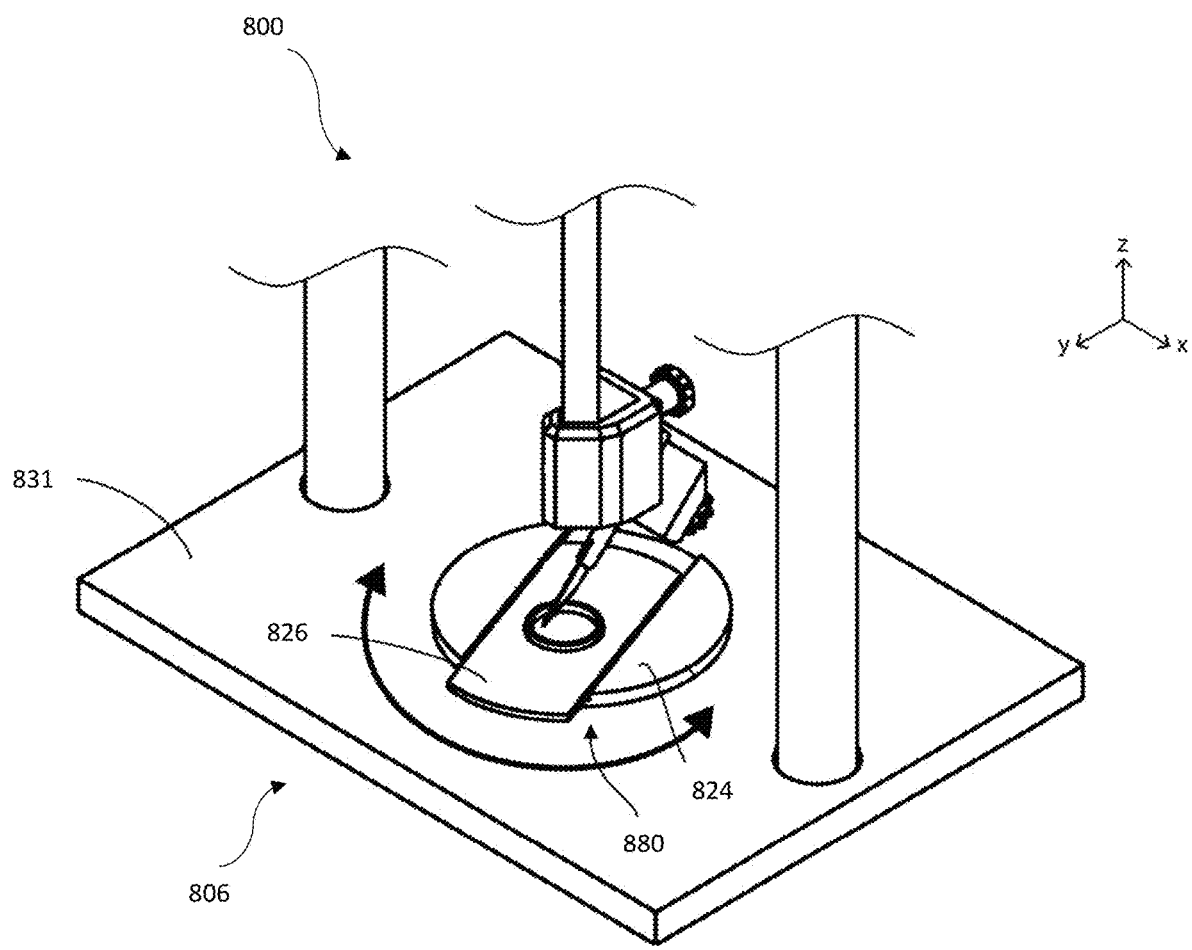
FIG. 9 depicts an example of a perspective view of the lower portion of the apparatus of FIG. 1, in accordance with aspects of the present disclosure.

Referring now to FIGS. 8-9, an embodiment of a lower portion of an apparatus 800 is depicted. The apparatus 800 may include a base 806 having a top surface 831 with a plurality of guide rails 824 located on the top surface 831. The top surface 831 of the base 806 may include a rotating platform 880, where the rotating platform 880 may be affixed to the top surface 831 via a rotatable mechanical coupling such as, for example, bearings, turntables, or other coupling systems. The rotating platform 880 may be geometrically sized and shaped, or configured to rotate about or capable of rotating about an axis that extends perpendicular to the top surface 831. Further, the rotating platform 880 may include the plurality of guide rails 824 and a slot 833 geometrically sized and shaped, or configured to receive, or otherwise capable of receiving a biological-material-containment facility 826. The rotating platform 880 may facilitate rotating or otherwise adjusting the biological-material-containment facility 826 about the axis to obtain a desired angular positioning of biological material. The biological-material-containment facility 826 may include sides that are shaped to slidably communicate or otherwise engage walls of the slot 833 that are formed by the plurality of guide rails 824.

According to one embodiment, the apparatus 800 may further include an angular positioning system that may include one or more detent mechanisms. The detent mechanisms may be arranged as a circumscribed array on an underside or sides of the rotating platform 880. The one or more detent mechanisms may be geometrically sized and shaped, or configured to engage or capable of engaging or otherwise communicating with one or more corresponding detent engaging members of the base 806. The one or more detent mechanisms may be capable of positioning and locking the rotating platform 880 into a desired location in order to modify the biological material.

According to various embodiments, an apparatus such as those described herein may include one or more mechatronic means for positioning biological material for modification and/or mechatronic means for modifying the biological material. For instance, positioning of one or more elements of the apparatus may include a series of operations performed by an embedded or otherwise electrically controlled computer system that controls the mechatronic means. Advantageously, the apparatus may include a mechatronic system to facilitate repeatable positioning of biological material, which may be desirous for various scientific experiments. The mechatronic system may include the mechatronic means and may further include a stepper or one or more other electronic motors to position one or more elements of the apparatus. In particular, the mechatronic system may facilitate positioning, relative to a blade-coupling-member assembly, a biological-material-containment facility that may include biological material. For example, the mechatronic system may include one or more elements for positioning a positioning arm of the apparatus and fastening one or more fixation members to couple the positioning arm to a crossbar of the apparatus. In particular, the positioning arm may be positioned via rotation of a lead screw powered by a stepper motor. Further, the positioning arm may be slidably adjusted within a chamber of the crossbar such that the biological material may be excised via a linear path excision that is off-center from the concentric center point of the biological-material-containment facility (e.g. a circular reservoir, well, or other dish-shaped recess).

Further, the mechatronic system may facilitate modifying the biological material using a blade apparatus of the blade-coupling-member assembly by moving the biological-material-containment facility relative to the blade apparatus. For instance, the mechatronic system may include an electric motor for positioning the plurality of guide rails and the slot by, e.g., rotating a rotatable platform. In particular, the mechatronic system may facilitate aligning the biological-material-containment facility at a desired angular position, relative to the blade apparatus, and retain and/or modify the desired angular position as the biological material is modified. Further, the mechatronic system may facilitate sliding the biological-material-containment facility within the slot formed by the plurality of guide rails, where the sliding facilitates linear path excision of the biological material. Additionally, the mechatronic system may facilitate angularly rotating the biological-material-containment facility during an excising operation of the biological material such that the excising occurs in an angularly positioned linear path relative to the blade apparatus.

According to one embodiment, the mechatronic system may facilitate dispensing or otherwise depositing the biological material in the biological-material-containment facility. Additionally, the mechatronic system may facilitate removing the biological-material-containment facility from the apparatus.

Referring to FIG. 10, an example is depicted of a perspective view of an apparatus 900 for modifying biological material, wherein an X-stepper motor (or X-motor) 902 (see FIG. 11), a Y-stepper motor (or Y-motor) 904 and a Z-stepper motor (or Z-motor) 906 are used to modify biological material 907 in X, Y and Z directions 908, 910, 912 respectively, in accordance with aspects of the present disclosure. Apparatus 900 is an example of a mechatronic system as previously discussed herein.

Though the X-motor 902, Y-motor 904 and Z-motor 906 are illustrated herein as stepper motors, and alternatively referred to herein as the X-stepper motor, Y-stepper motor and Z-stepper motor, it is within the scope of this disclosure that the X-motor 902, Y-motor 904 and Z-motor 906 may be other types of motors as well. For example, the X, Y and Z-motors 902, 904, 906 may be a servo motor or a DC driven motor. Also, by way of example, the X, Y and Z-motors 902, 904, 906 may be virtually any type of motor that can be interfaced with an encoder to enable the Apparatus 900 to generate electronically encoded position information regarding the motor.

The apparatus 900 includes a base 914, a frame 916 and an adjustable arm assembly 918. The base 914 includes a first guide rail 920 and a second guide rail 922 that are substantially disposed in parallel on a top surface 924 of the base 914. The first and second guide rails 920, 922 define a slot 926 therebetween. A biological-material containment facility 928 is configured to fit within the slot 926. The containment facility 928 is operable to be guided in the X direction 908 by the first and second guide rails 920, 922.

The frame 916 includes a first support 930 and a second support 932 attached to the base 914. The first and second supports 930, 932 of the frame 916 straddle the first and second guide rails 920, 922.

A crossbar (or crossbar assembly) 934 extends between the first and second supports 930, 932. The crossbar 934 includes a crossbar body 936 that extends between the first and second supports 930, 932. The crossbar body includes block shaped first and second end portions 938 and 940 that are coupled to the upper end portions of the first and second supports 930. The crossbar assembly 934 also includes the Y-stepper motor 904, which is mounted to the first crossbar end portion 938. The Y-stepper motor 094 is mechanically coupled to a Y-lead screw 942 that is extending in the Y-direction 910, wherein the Y-direction is substantially perpendicular to the X direction 908.

The adjustable arm assembly 918 is engaged with the Y-lead screw 942 such that the arm assembly 918 traverses in the Y direction 910 when the Y-stepper motor 904 turns the Y lead screw 942. More specifically, the arm assembly 918 includes a Y-carriage block 944 that is threadedly engaged to the Y-lead screw 942 of the crossbar 934. The Y-carriage block is operable to traverse the Y-lead screw 942 in the Y direction 910 when the Y-lead screw 942 is turned by the Y-stepper motor 904.

Figure 10:
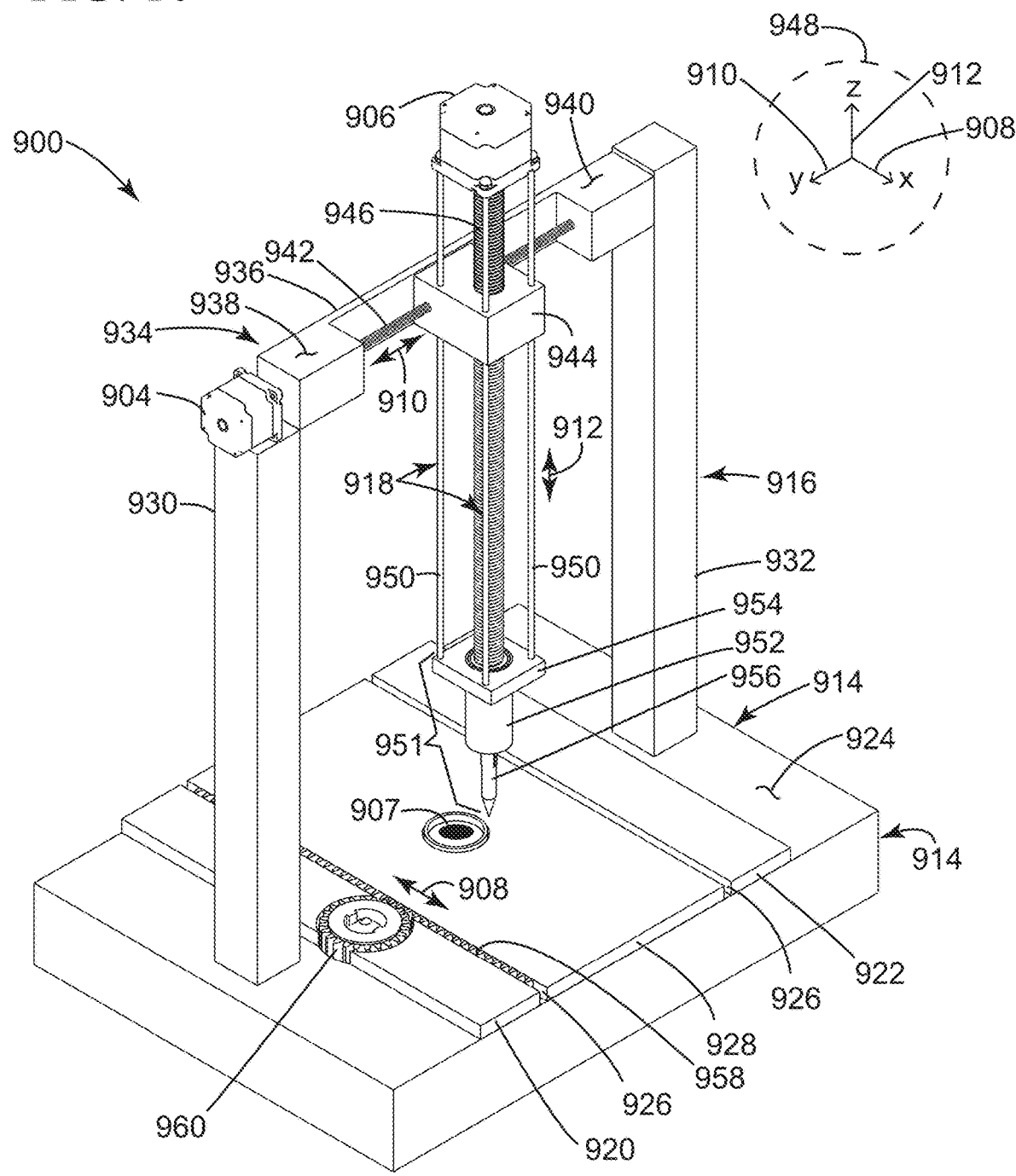
FIG. 10 depicts an example of a perspective view of an apparatus for modifying biological material, wherein X, Y and Z stepper motors are used to modify biological material in an X, Y and Z direction respectively, in accordance with aspects of the present disclosure.

A Z-lead screw 946 is threadedly engaged with the Y-carriage block 944. The Z-lead screw 946 of FIG. 10 is similar in function to the positioning arm 121 of FIG. 1. The Z-lead screw 946 extends in a Z direction 912 that is substantially perpendicular to an X-Y plane defined by the X and Y directions 908, 910 (see coordinate diagram 948). The Z-stepper motor 906 is mounted on four guide rods 950, which extend through, and are rigidly attached to, the Y-carriage block 944. The Z-stepper motor 906 is also mechanically coupled to an upper distal end of the Z-lead screw 946.

The adjustable arm assembly 918 also includes a blade-coupling member assembly 951. The blade-coupling member assembly 951 of FIG. 10 is similar in function to the blade-coupling member assembly 114 of FIG. 1. The blade-coupling member assembly 951 includes a blade adapter 952 and a blade 956.

The blade adapter 952 of the blade-coupling member assembly is threadedly engaged to a lower distal end of the Z-lead screw 946. The blade adapter 952 includes a Z-carriage plate 954, which is slidably connected to lower portions of the four guide rods 950. The blade adapter 952 is operable to traverse the Z-lead screw 946 in the Z direction 912, when the Z-lead screw 946 is turned by the Z-stepper motor 906. As the blade adapter rides up and down on the Z-lead screw 946, the guide rods 950 slide through and guide the Z-carriage plate 954 of the blade adapter 952 to allow for movement of the blade adapter 952 in the Z direction 912.

The blade 956 is mechanically coupled to the lower portion of the blade adapter 952. The blade 956 extends downward from the blade adapter 952 toward the containment facility 928. The blade 956 is operable to engage a biological material 907 disposed on the containment facility 928.

Advantageously, the blade 956 is operable to modify (for example, cut or wound) the biological material 907 in the Y-direction 910 when the Y-stepper motor 904 turns the Y-lead screw 942 to move the arm assembly 918 in the Y-direction 910. Additionally advantageously, the blade is operable to modify the biological material 907 in the Z-direction 912 when the Z-stepper motor 906 turns the Z-lead screw 946 to move the blade adapter 952 and blade 956 in the Z-direction 912.

Also advantageously, the blade 956 is operable to modify the biological material 907 in the X-direction 908 when the containment facility 928 is moved within the slot 926 in the X direction 908. The movement of the containment facility 928 in the X-direction 908 may be accomplished by hand, using the sides of the first and second guide rails 920, 922 as guides. Alternatively, as will be discussed in greater detail with regards to FIG. 11, the movement of the containment facility 928 in the X-direction 908 may be accomplished via X-stepper motor 902.

The blade 956 may be a variety of cutting tools or cutting blades. For example, the blade 956 may be a 360 degree cutting tool, which is operable to swivel 360 degrees to provide multi-directional cuts in any of the X, Y or Z directions. The blade 956 may be any number of cutting tools available on the market, or may be specially made to order. For example, the blade may be 3D printed to specific specifications.

Figure 11:
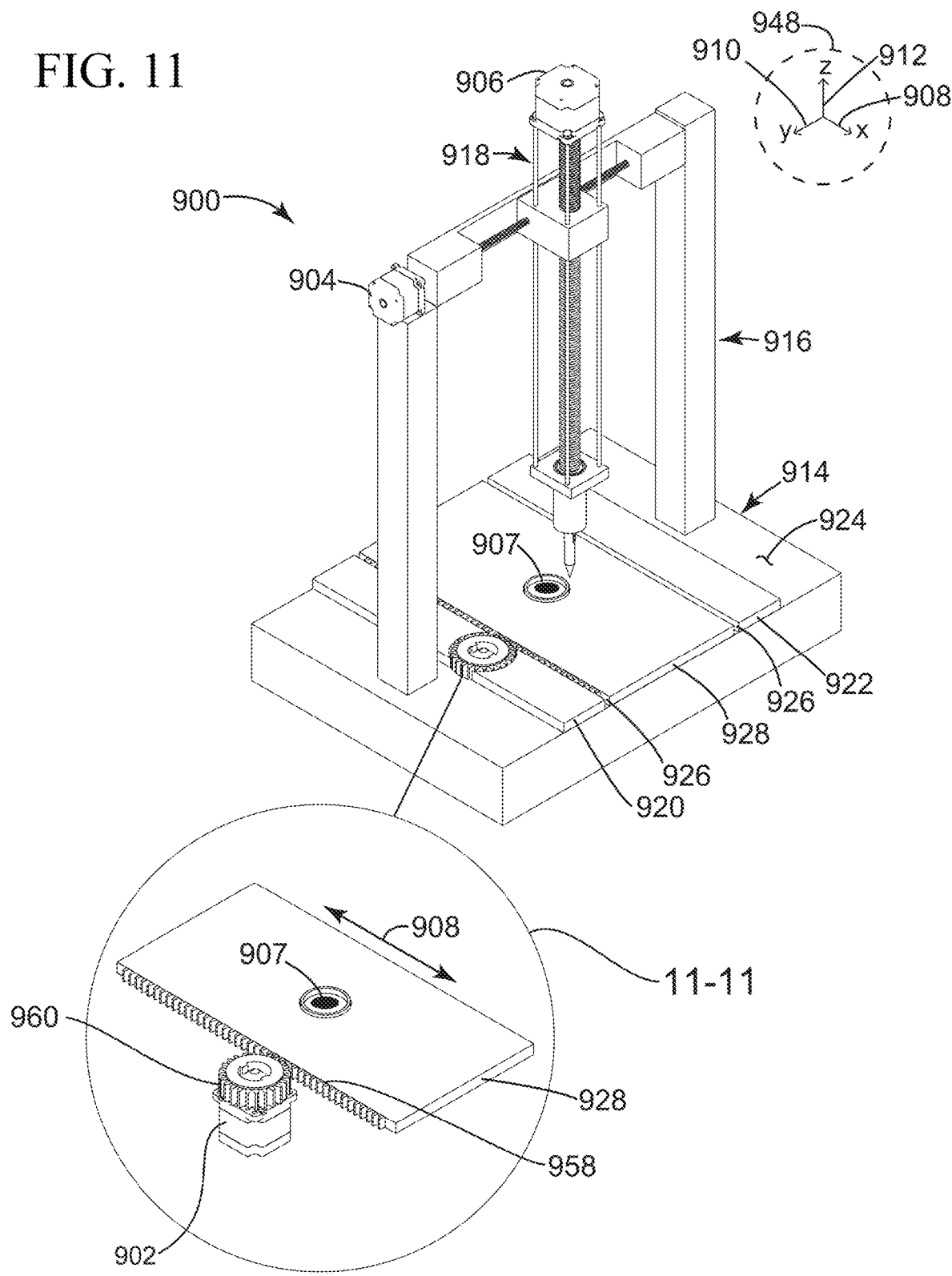
FIG. 11 depicts an example of the perspective view of FIG. 10 with an enlarged view of an X direction rack gear and pinion gear within a circle 11-11, in accordance with aspects of the present disclosure.

Referring to FIG. 11, an example is depicted of the perspective view of the apparatus 900 with an enlarged view of an X-rack gear 958 and an X-pinion gear 960 within a circle 11-11, in accordance with aspects of the present disclosure. The X-pinion gear 960 is disposed over or on the top surface 924 of the base 914. In the example illustrated in FIG. 11, the X-pinion gear 960 is disposed within the first guide rail 920 of the pair of first and second guide rails 920, 922. However, it is within the scope of this disclosure that the X-pinion gear 960 may be disposed in other locations as well. For example, on or over the second guide rail 922.

The X-stepper motor 902 is mechanically coupled to the X-pinion gear 960. The X-stepper motor 902 is rigidly mounted to the underside of the base 914.

The X-rack gear 958 is disposed on a side of the biological-material containment facility 928. The X-rack gear 958 is operable to mesh with the X-pinion gear 960 when the containment facility 928 is disposed within the slot 926 that is defined by the first and second guide rails 920, 922. Accordingly, the containment facility 928 is moved within the slot 926 in the X direction 908 when the X-rack gear 958 is meshed with the X-pinion gear 960 and the X-stepper motor 902 turns the X-pinion gear 960.

Figure 12:
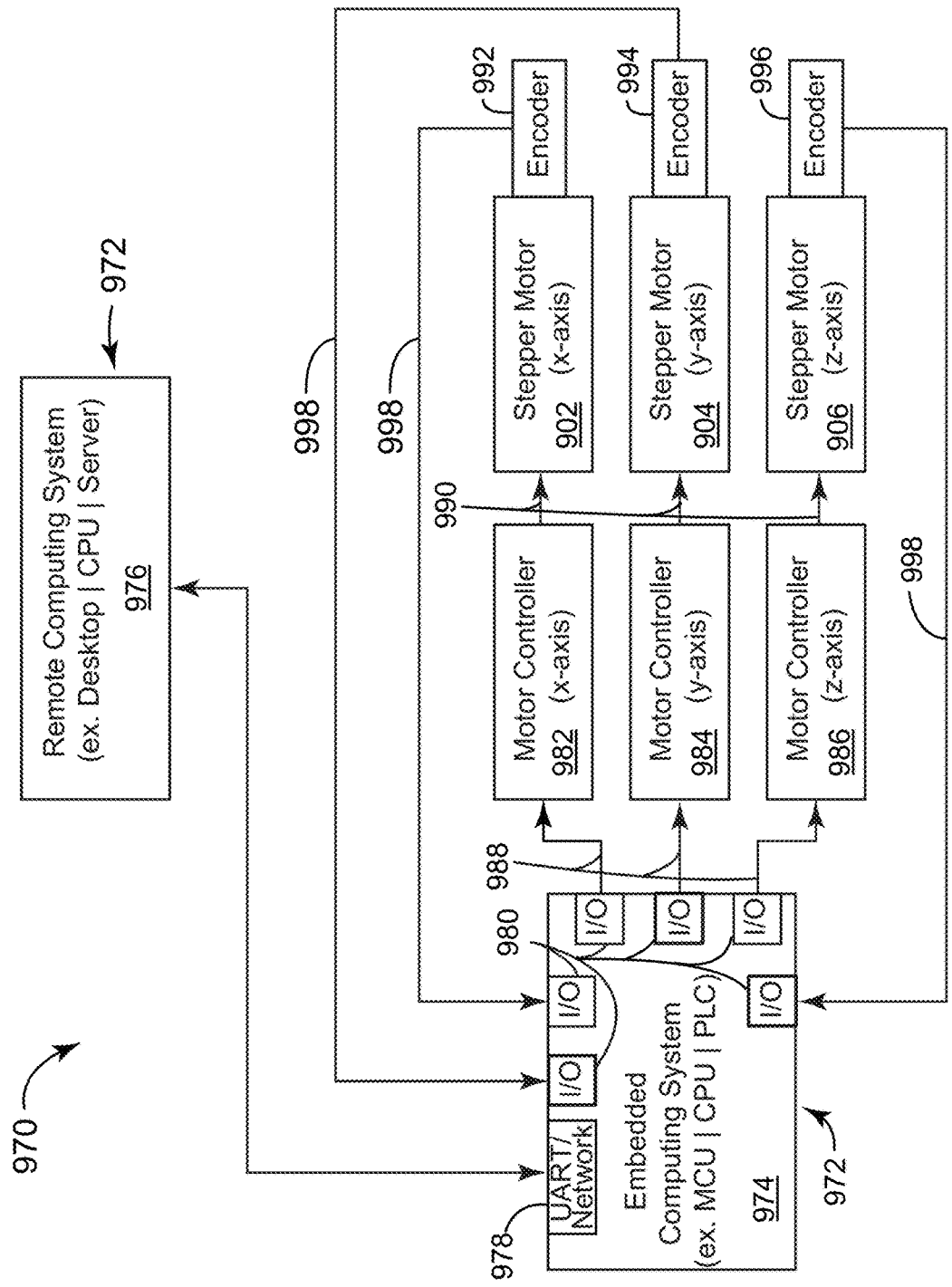
FIG. 12 depicts an example of a block diagram of a computerized control system for controlling the X, Y and Z stepper motors of FIG. 10, in accordance with aspects of the present disclosure.

Referring to FIG. 12, an example is depicted of a block diagram of a computerized control system 970 for controlling the X, Y and Z stepper motors 902, 904, 906 of FIG. 10, in accordance with aspects of the present disclosure. The computerized control system 970 may include a computing system 972. The computing system may include, without limitation, a variety of such devices as a central processing unit (CPU), a programmable logic controller (PLC) and/or a microcontroller (MCU).

The computing system 972 may include both or either an embedded computing system 974 and a remote computing system 976. In the example illustrated in FIG. 12, the computing system 972 includes both an embedded computing system 974 and a remote computing system 976. The remote and embedded computing systems may be in electrical communication with each other via a communication device 978. The communication device 978 may be, for example, a universal asynchronous receiver-transmitter (UART) or other similar devices or systems. The embedded computing device 974 may control such automated devices as motor controllers, encoders and stepper motors. The remote computing device 976 may provide input information to the embedded computing device 972.

In the computerized control system 970 of FIG. 12, an X-motor controller 982, a Y-motor controller 984 and a Z-motor controller 986 are in electrical communication with, and receive data from, the embedded computing system 974 via input/output ports 980. The X, Y and Z-motor controllers 982, 984, 986 are also in electrical communication with the X-stepper motor 902, the Y-stepper motor 904 and the Z-stepper motor 906 respectively. Each of the motor controllers 982, 984, 986 are operable to receive a first set of control signals 988 from the embedded computing system 974 of the computing system 972. Each of the motor controllers 982, 984, 986 are also operable to generate a second set of control signals 990 to each of their respective stepper motors 902, 904, 906. The first and second set of control signals 988, 990 provide information that is indicative of modifications to the biological material 907 to be made by the blade 956 in the X, Y and Z directions 908, 910, 912.

An X-encoder 992, a Y-encoder 994 and a Z encoder 996 are mechanically coupled to the X-stepper motor 902, Y-stepper motor 904 and Z-stepper motor 906, respectively. Each of the encoders 992, 994, 996 are operable to generate position signals 998 to the computing system 972. The position signals 998 are indicative of position information of the blade 956 relative to the biological material 907.

Advantageously, the computerized control system 970 enables the apparatus 900 to modify a plurality of biological materials 907 by cutting each of the plurality of biological materials 907 with a substantially same pattern of cuts in the X direction 908, the Y direction 910 and the Z direction 912. In other words, complex patterns of cuts in the X, Y and Z directions on a several different biological materials 907 may be repeatedly made with a degree of precision and repeatability that cannot be duplicated by a human hand. This has advantages in researching such issues as, for example, how wounds heal and how best to cut a biological sample to enable optimal healing.

Figure 13:
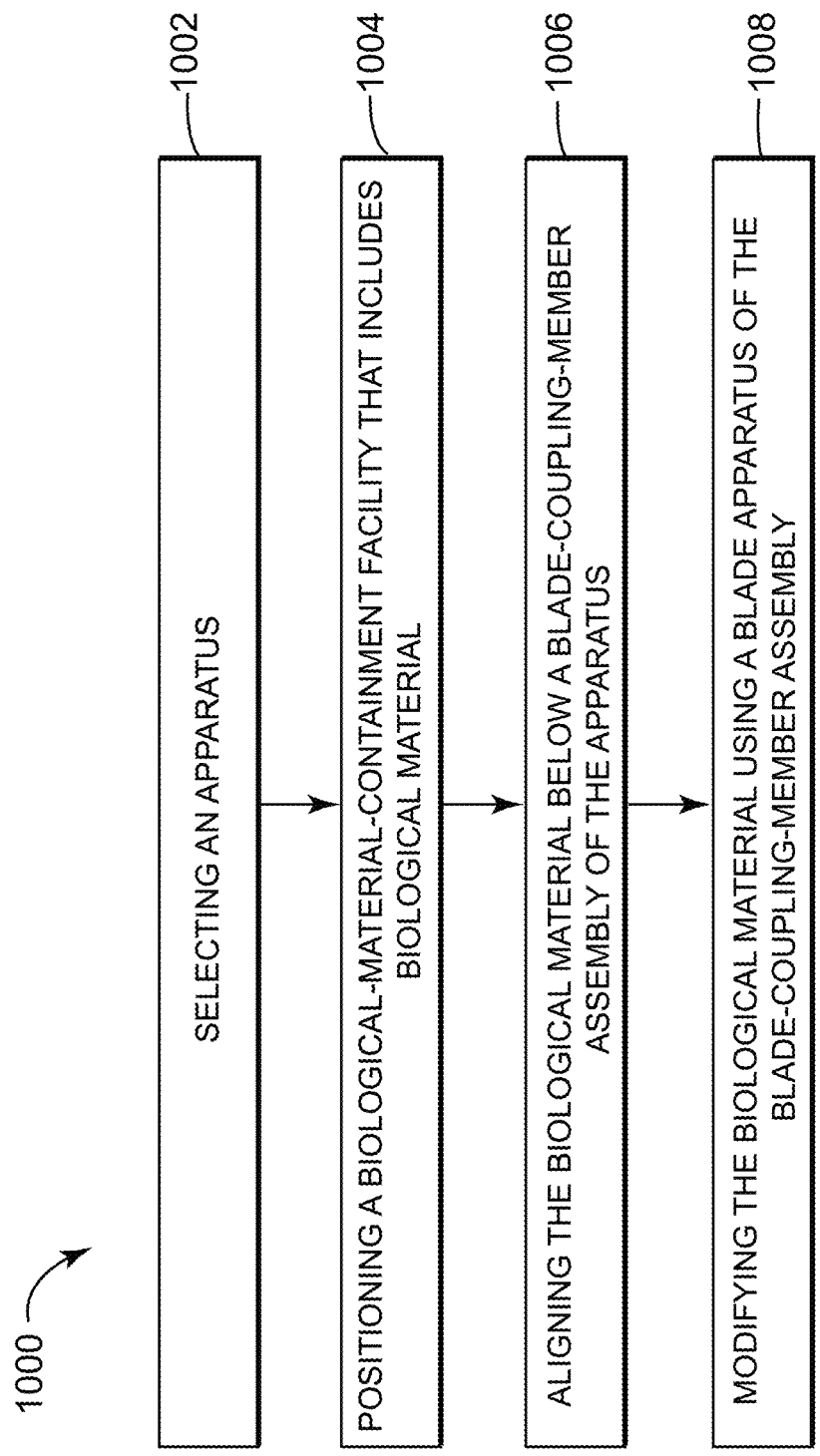
FIG. 13 depicts an example of a flowchart depicting a method of modifying biological material, in accordance with aspects of the present disclosure.

FIG. 13 is a flowchart depicting the example steps of method 1000 for modifying biological material in accordance with aspects described herein. The method 1000 includes selecting 1002 an apparatus and positioning 1004 a biological-material-containment facility that includes the biological material, the positioning includes aligning 1006 the biological material below a blade-coupling-member assembly of the apparatus. Further, the method may include depositing biological material in the biological-material-containment facility. The method 1000 may also include modifying 1008 the biological material using a blade apparatus of the blade-coupling-member assembly. According to one embodiment, the apparatus may include a plurality of guide rails, and the positioning may include rotating the plurality of guide rails about an axis. Additionally, the method 1000 may include adjusting a location of a positioning arm for desired orientation, where the adjusting may include aligning the positioning arm within a channel of a crossbar of a frame of the apparatus and fixating, via one or more fasteners, the positioning arm to the crossbar in the desired orientation.

Figure 14:
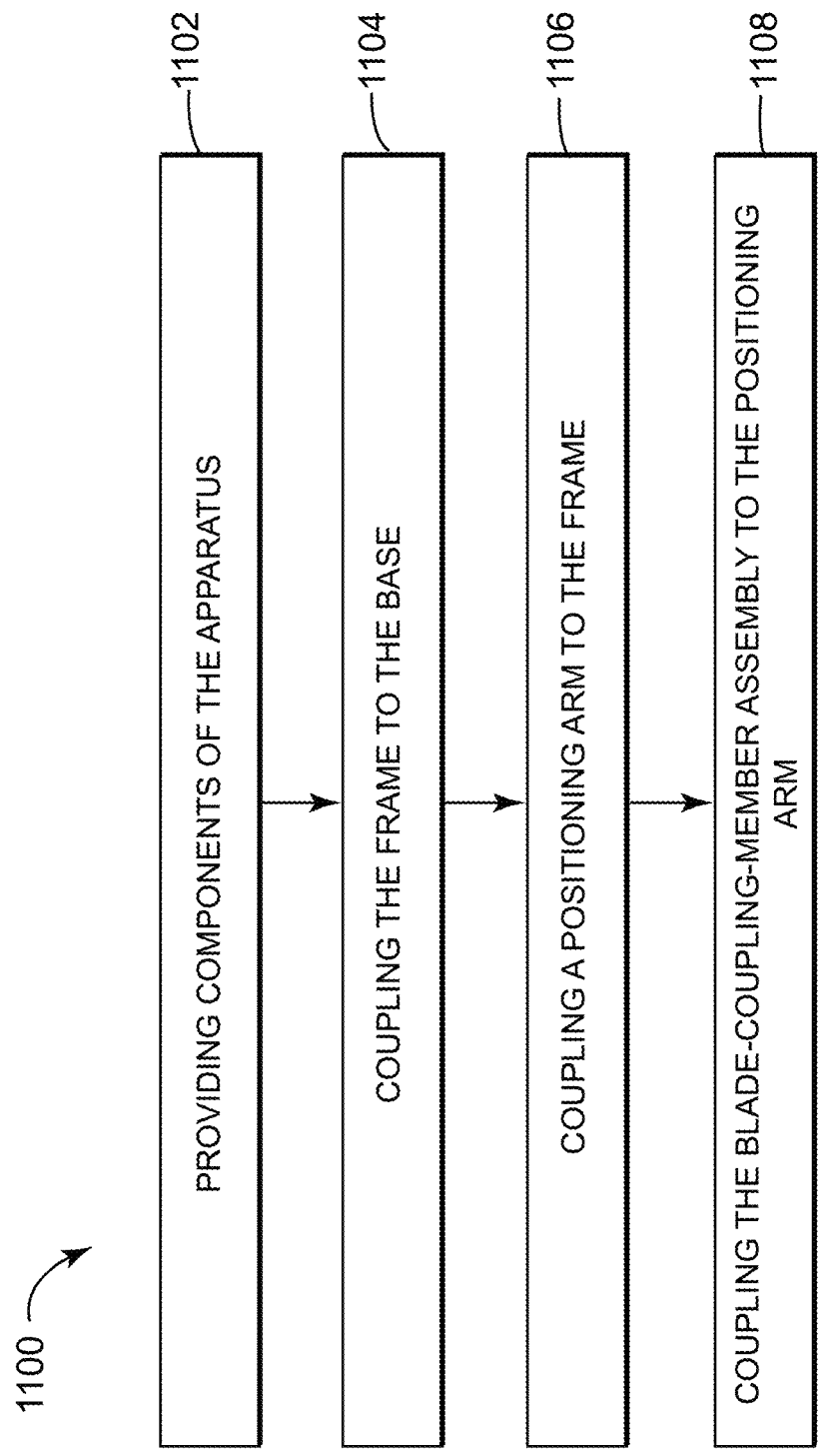
FIG. 14 depicts an example of a flowchart depicting a method of assembling an apparatus for modifying biological material, in accordance with aspects of the present disclosure.

FIG. 14 is a flowchart showing the example steps of method 1100 for assembling an apparatus. The method 1100 includes providing 1102 components of the apparatus, where the components include a base, a frame, and an adjustable arm assembly. Further, the adjustable arm assembly includes a positioning arm extending from a first arm end to a second arm end and a blade-coupling-member assembly. Further, the method 1100 includes coupling 1104 the frame to the base. According to one embodiment, the method may also include coupling 1106 the positioning arm to the frame. Additionally, the method may include coupling 1108 the blade-coupling-member assembly to the positioning arm.

Referring to FIG. 15A, an example is depicted of a flow diagram of a method 1200 of modifying biological material, in accordance with aspects of the present disclosure. At 1202, the method 1200 provides an apparatus 900 for modifying biological material 907.

The apparatus 900 includes a base 914, which includes first and second guide rails 920, 922 disposed on a top surface 924 of the base 914. The guide rails 920, 922 define a slot 926 therebetween, wherein the slot 926 extends in an X-direction 908.

The apparatus 900 also includes a frame 916. The frame 916 includes first and second supports 930, 932 attached to the base 914 and straddling the first and second guide rails 920, 922. The frame 916 also includes a crossbar 934 (or crossbar assembly), which extends between the first and second guide rails 920, 922 in a Y direction 910 that is substantially perpendicular to the X direction 908.

The apparatus 900 also includes an adjustable arm assembly 918 attached to the crossbar 934. The arm assembly 918 extends downward from the crossbar 934 toward the base 914 in a Z direction 912 that is substantially perpendicular to an X-Y plane defined by the X and Y directions. The arm assembly 918 includes a blade 956 mechanically coupled to a lower end portion of the arm assembly 918.

At 1204, a biological-material containment facility 928 is positioned in the slot 926. The containment facility 928 is operable to be guided by the first and second guide rails 920, 922 in the X direction 908.

At 1206, a biological material 907 is disposed (i.e., positioned) on the containment facility 928.

At 1208, the biological material 907 is engaged with the blade 956.

At 1210, the biological material 907 is modified in the X direction 908 by moving the containment facility 928 within the slot 926 between the first and second guide rails 920, 922.

At 1212, the biological material 907 is modified in the Y direction 910 by traversing the adjustable arm assembly 918 along the crossbar 934.

At 1214, the biological material 907 is modified in the Z direction 912 by adjusting the adjustable arm assembly 918 to vary a distance of the blade 956 above the base 914 in the Z direction 912.

Referring to FIG. 15B, an example is depicted of a continuation of the flow diagram of the method 1200 illustrated in FIG. 15A, in accordance with aspects of the present disclosure. FIG. 15B is a subset of FIG. 15A and describes further steps that may be taken in method 1200.

At 1216, the containment facility 928 is driven within the slot 926 in the X direction 908 with an X-stepper motor 902. This enables machine or mechatronic modifications of the biological material 907 (such as cuts) in the X direction 908.

At 1218, the adjustable arm assembly 918 is driven along the crossbar 934 in the Y direction 910 with a Y-stepper motor 904. This enables machine or mechatronic modification of the biological material 907 (such as cuts) in the Y direction 910.

At 1220, the adjustable arm assembly 918 is driven to vary a distance of the blade 956 above the base 914 in the Z direction 912 with a Z-stepper motor 906. This enables machine or mechatronic modifications of the biological material 907 (such as cuts) in the Z direction 912.

At 1222, a plurality of biological materials 907 are modified by cutting each of the plurality of biological materials 907 with a substantially same pattern of cuts in the X direction 908, the Y direction 910 and the Z direction 912. Advantageously, the mechatronic features of the apparatus 900 enables complex patterns of cuts in the X, Y and Z directions on several different biological materials 907. The complex patterns may be repeatedly made with a degree of precision and repeatability that cannot be duplicated by a human hand. This has advantages in researching such issues as, for example, how wounds heal and how best to cut a biological sample to enable optimal healing thereafter.

Although various examples are provided, variations are possible without departing from a spirit of the claimed aspects.

Although various embodiments are described above, these are only examples. The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing"), when used in this specification, specify the presence of stated features, integers, steps, operations, elements, and/or components, but do not preclude the presence or addition of one or more other features, integers, steps, operations, elements, components, and/or groups thereof. As a result, a device or structure that is configured in a certain way is configured in at least that way, but may also be configured in ways that are not listed.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable or suitable. For example, in some circumstances, an event or capacity can be expected, while in other circumstances the event or capacity cannot occur—this distinction is captured by the terms "may" and "may be."

The terms "connect," "connected," "contact," "coupled" and/or the like are broadly defined herein to encompass a variety of divergent arrangements and assembly techniques. These arrangements and techniques include, but are not limited to (1) the direct joining of one component and another component with no intervening components therebetween (i.e., the components are in direct physical contact); and (2) the joining of one component and another component with one or more components therebetween, provided that the one component being "connected to," "contacting" or 'coupled to" the other component is somehow in operative communication (e.g., electrically, fluidly, physically, optically, etc.) with the other component (notwithstanding the presence of one or more additional components therebetween). It is to be understood that some components that are in direct physical contact with one another may or may not be in electrical contact and/or fluid contact with one another. Moreover, two components that are electrically connected, electrically coupled, optically connected, optically coupled, fluidly connected or fluidly coupled may or may not be in direct physical contact, and one or more other components may be positioned therebetween.

Moreover, as used herein, the terms "first," "second," and "third," etc. are used merely as referee labels, and are not intended to impose numerical, structural or other requirements on their objects. Forms of term "based on" herein encompass relationships where an element is partially based on as well as relationships where an element is entirely based on.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description, but is not intended to be exhaustive or limited to in the form disclosed. Many modifications and variations will be apparent to those of ordinary skill in the art. The embodiment was chosen and described in order to best explain various aspects and the practical application, and to enable others of ordinary skill in the art to understand various embodiments with various modifications as are suited to the particular use contemplated.

It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed is:

1. An apparatus for modifying biological material, the apparatus comprising:
 a base;
 a frame coupled to the base, the frame comprising,
  a first support coupled to a first end of the base,
  a second support coupled to a second end of the base, and
  an adjustable cross-bar assembly extending between the first and second supports and positioned above the base, the adjustable cross-bar assembly comprising:
   a cross-bar body extending from a first end portion of the cross-bar body to a second end portion of the cross-bar body, wherein the first end portion is coupled to the first support, and wherein the second end portion is coupled to the second support;
   a blade-coupling-member assembly coupled to the cross-bar body via a Z-lead screw, the blade-coupling member assembly threadingly engaged to a lower distal end of the Z-lead screw, the blade-coupling member assembly comprising a blade and a blade adapter, wherein the blade adapter includes a Z-carriage plate through which the Z-lead screw extends;
  a first guide rail and a parallel second guide rail located on a top surface of the base, the first and second guide rails extending horizontally relative to the top surface of the base and defining a slot therebetween;
  a biological-material-containment facility configured to be received within the slot and to contain biological material;
  an X-rack gear disposed on a side of the biological-material-containment facility and affixed thereto;
  an X-pinion gear configured to bifurcate the first guide rail, the first guide rail disposing within and partially enclosing the X-pinion gear on the top surface of the base, the X-pinion gear configured to mesh with the X-rack gear to linearly drive the biological-materialcontainment facility in a horizontal direction within the slot, guided by the first and second guide rails; and an X-motor mechanically coupled to the X-pinion gear and mounted to an underside of the base, opposite the top surface of the base, the X-motor configured to rotationally drive the X-pinion gear;

wherein the blade-coupling-member assembly is suspended above the slot; and wherein the blade is configured to modify the biological material as the biological-material containment facility is moved horizontally within the slot.

2. The positioning apparatus of claim 1, wherein the biological-material-containment facility is a sliderplate.

3. The apparatus of claim 1, wherein the first guide rail and the second guide rail are perpendicular to the crossbar body of the frame.

4. The apparatus of claim 1, wherein the crossbar assembly comprises:

a Y-lead screw, wherein the Y-lead screw facilitates movement of an adjustable arm assembly; and wherein the blade-coupling-member assembly is coupled to the adjustable arm assembly.

5. The apparatus of claim 4, wherein the adjustable arm assembly comprises at least one guide rod.

6. The apparatus of claim 5, wherein the adjustable arm assembly comprises a plurality of guide rods.

7. The apparatus of claim 5, wherein the plurality of guide rods is four guide rods.

8. The apparatus of claim 4, wherein the adjustable arm assembly further comprises a Z-lead screw and a Y-carriage block, wherein the Z-lead screw threadingly couples to the Y-carriage block.

9. The apparatus of claim 8, wherein the location of the blade-coupling-member assembly is adjustable along a longitudinal axis of the Z-lead screw and a longitudinal axis of the Y-lead screw.

10. An apparatus for modifying biological material, the apparatus comprising:

a base, comprising:

a first and a second guide rail substantially disposed in parallel on a top surface of the base and defining a slot therebetween;

a biological-material containment facility configured to fit within the slot and operable to be guided in an X direction that is parallel to the first and second guide rails and extends horizontally relative to the top surface of the base;

an X-rack gear disposed on a side of the biological-material-containment facility and affixed thereto;

an X-pinion gear configured to bifurcate the first guide rail, the first guide rail disposing within and partially enclosed enclosing the X-pinion gear on the top surface of the base, the X-pinion gear configured to mesh with the X-rack gear to linearly drive the biological-material-containment facility in a horizontal direction within the slot, guided by the first and second guide rails;

an X-motor mechanically coupled to the X-pinion gear and mounted to the underside of the base, opposite the top surface of the base, the X-motor configured to rotationally drive the X-pinion gear;

a frame comprising:

first and second supports attached to the base and straddling the first and second guide rails, and a crossbar assembly extending between the first and second supports, the crossbar assembly comprising a Y-motor that is mechanically coupled to a Y-lead screw that is extending in a Y-direction that is substantially perpendicular to the X direction and extends horizontally relative to the top surface of the base; and an adjustable arm assembly engaged with the Y-lead screw such that the adjustable arm assembly traverses in the Y direction when the Y-motor turns the Y lead screw, the adjustable arm assembly comprising:

a Z-lead screw, and a blade-coupling member assembly threadingly engaged to a lower distal end of the Z-lead screw, the blade-coupling member assembly comprising:

a blade adapter, wherein the blade adapter includes a Z-carriage plate through which the Z-lead screw extends, and a blade operable to engage a biological material disposed on the containment facility;

wherein the blade is operable to modify the biological material in the Y-direction, when the Y-motor turns the Y-lead screw to move the adjustable arm assembly in the Y-direction; and wherein the blade is operable to modify the biological material in the X-direction when the containment facility is moved within the slot in the X direction.

11. The apparatus of claim 10, wherein the adjustable arm assembly comprises:

a Y-carriage block threadedly engaged to the Y-lead screw of the crossbar, the Y-carriage block is operable to traverse the Y-lead screw in the Y direction when the Y-lead screw is turned by the Y-motor;

a Z-lead screw engaged with the Y-carriage block and extending in a Z direction that is substantially perpendicular and vertical relative to the top surface of the base;

a Z-motor mechanically coupled to an upper distal end of the Z-lead screw;

the blade-coupling member assembly further comprising a blade adapter, the blade adapter threadedly engaged to a lower distal end of the Z-lead screw, the blade adapter operable to traverse the Z-lead screw in the Z direction when the Z-lead screw is turned by the Z-motor; and the blade mechanically coupled to the lower portion of the blade adapter, the blade extending downward from the blade adapter toward the containment facility;

wherein the blade is operable to modify the biological material in the Z-direction when the Z-motor turns the Z-lead screw to move the blade adapter in the Z-direction.

12. The apparatus of claim 11, comprising:

an X-pinion gear disposed within the first guide rail and on the top surface of the base;

an X-motor mechanically coupled to the X-pinion gear and mounted to the underside of the base, the X-motor configured to rotationally drive the X-pinion gear;

an X-rack gear disposed on a side of the biological-material containment facility and affixed thereto, the X-rack gear operable to mesh with the X-pinion gear when the containment facility is disposed within the slot; and wherein the containment facility is moved linearly within the slot in the X direction when the X-rack gear is meshed with the X-pinion gear and the X-motor turns the X-pinion gear.

13. The apparatus of claim 12, comprising:

a computing system;

an X-motor controller, a Y-motor controller and a Z-motor controller in electrical communication with the X-motor, Y-motor and Z-motor respectively, each of the motor controllers operable to receive a first set of control signals from the computing system and to generate a second set of control signals to each of their respective motors, the first and second set of control signals being indicative of modifications to the biological material to be made by the blade in the X, Y and Z directions; and an X-encoder, a Y-encoder and a Z encoder mechanically coupled to the X-motor, Y-motor and Z-motor respectively, each of the encoders operable to generate position signals to the computing system, the position signals being indicative of position information of the blade relative to the biological material.

14. The apparatus of claim 13, wherein the apparatus is operable to modify a plurality of biological materials by cutting each of the plurality of biological materials with a substantially same pattern of cuts in the X direction, Y direction and Z direction.

15. A method of modifying biological material, the method comprising:
providing an apparatus for modifying biological material, the apparatus comprising:
a base comprising first and second guide rails disposed on a top surface of the base and defining a slot therebetween, the slot extending in an X-direction that is horizontal to the top surface to the base,
a biological-material containment facility configured to fit within the slot and operable to be guided in an X direction that is parallel to the first and second guide rails and extends horizontally relative to the top surface of the base,
an X-rack gear disposed on a side of the biological-material-containment facility and affixed thereto,
an X-pinion gear configured to bifurcate the first guide rail, the first guide rail disposing within and partially enclosing the X-pinion gear on the top surface of the base, the X-pinion gear configured to mesh with the X-rack gear to linearly drive the biological-material-containment facility in a horizontal direction within the slot, guided by the first and second guide rails,
an X-motor mechanically coupled to the X-pinion gear and mounted to the underside of the base, opposite the top surface of the base, the X-motor configured to rotationally drive the X-pinion gear,
a frame comprising first and second supports attached to the base and straddling the first and second guide rails, and further comprising a crossbar assembly extending between the first and second guide rails in a Y direction that is substantially perpendicular to the X direction and extends horizontally relative to the top surface of the base, and
an adjustable arm assembly attached to the crossbar assembly, the adjustable arm assembly extending downward from the crossbar assembly toward the base in a Z direction that is substantially perpendicular and vertical relative to the top surface of the base, the adjustable arm assembly comprising a Z-lead screw coupled a blade-coupling member assembly, the blade-coupling member assembly comprising a blade and a blade adapter, wherein the blade adapter includes a Z-carriage plate through which the Z-lead screw extends;

positioning the biological-material containment facility in the slot;
disposing a biological material on the containment facility;
engaging the biological material with the blade;
modifying the biological material in the X direction by moving the containment facility within the slot between the first and second guide rails;
modifying the biological material in the Y direction by traversing the adjustable arm assembly along the crossbar; and
modifying the biological material in the Z direction by adjusting the adjustable arm assembly to vary a distance of the blade above the base in the Z direction.

16. The method of claim 15, comprising:
the providing the apparatus further comprising:
an X-pinion gear disposed within the first guide rail and on the top surface of the base,
an X-motor mechanically coupled to the X-pinion gear and mounted to the underside of the base, the X-motor configured to rotationally drive the X-pinion gear, and
an X-rack gear disposed on a side of the biological-material containment facility and affixed thereto, the X-rack gear operable to mesh with the X-pinion gear when the containment facility is disposed within the slot;
driving the containment facility within the slot in the X direction with the X-motor;
driving the adjustable arm assembly along the crossbar in the Y direction with a Y-motor; and
driving the adjustable arm assembly to vary a distance of the blade above the base in the Z direction with a Z-motor.

17. The method of claim 16, comprising:
modifying a plurality of biological materials by cutting each of the plurality of biological materials with a substantially same pattern of cuts in the X direction, Y direction and Z direction.

* * * * *